US011828683B2

(12) United States Patent
Dysinger et al.

(10) Patent No.: US 11,828,683 B2
(45) Date of Patent: Nov. 28, 2023

(54) METHOD OF QUANTITATING UNBOUND C5A IN A SAMPLE

(71) Applicant: Alexion Pharmaceuticals, Inc., Boston, MA (US)

(72) Inventors: Mark Dysinger, Killingworth, CT (US); Mark Ma, Madison, CT (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 1074 days.

(21) Appl. No.: 16/342,217

(22) PCT Filed: Oct. 19, 2017

(86) PCT No.: PCT/US2017/057377
§ 371 (c)(1),
(2) Date: Apr. 16, 2019

(87) PCT Pub. No.: WO2018/075761
PCT Pub. Date: Apr. 26, 2018

(65) Prior Publication Data
US 2019/0242893 A1  Aug. 8, 2019

Related U.S. Application Data

(60) Provisional application No. 62/410,028, filed on Oct. 19, 2016.

(51) Int. Cl.
*G01N 33/564* (2006.01)
*G01N 33/543* (2006.01)
*C07K 16/36* (2006.01)

(52) U.S. Cl.
CPC .......... *G01N 33/564* (2013.01); *C07K 16/36* (2013.01); *G01N 33/54326* (2013.01); *G01N 33/54366* (2013.01)

(58) Field of Classification Search
None
See application file for complete search history.

(56) References Cited

U.S. PATENT DOCUMENTS

| | | | |
|---|---|---|---|
| 6,319,469 B1* | 11/2001 | Mian | B01L 3/50273 422/63 |
| 2002/0015957 A1* | 2/2002 | Hageman | A61P 37/02 351/200 |
| 2003/0175267 A1* | 9/2003 | Wang | A61P 29/00 530/389.3 |
| 2006/0067935 A1* | 3/2006 | Ambati | C07K 14/70596 514/44 A |
| 2010/0173793 A1* | 7/2010 | Dilly | G01N 33/6845 506/18 |
| 2011/0014182 A1* | 1/2011 | Alard | A61P 27/12 514/17.8 |
| 2014/0056878 A1* | 2/2014 | McConnell | C07K 16/18 435/328 |
| 2016/0263126 A1 | 9/2016 | Kulikowski et al. | |
| 2016/0266136 A1 | 9/2016 | Cochran et al. | |
| 2019/0250157 A1 | 8/2019 | Dysinger et al. | |
| 2019/0276524 A1 | 9/2019 | Griffin et al. | |

FOREIGN PATENT DOCUMENTS

| | | | |
|---|---|---|---|
| CA | 2797856 | * | 4/2011 |
| EP | 0097440 A1 | | 1/1984 |
| JP | S595958 B2 | | 2/1984 |
| JP | 2010-151738 A | | 7/2010 |
| JP | 2016-520542 A | | 7/2016 |
| WO | WO 2005072380 | * | 8/2005 |
| WO | 2008/140483 A2 | | 11/2008 |
| WO | 2011/137395 A1 | | 11/2011 |
| WO | WO 2012088247 | * | 12/2011 |
| WO | 2012/045451 A1 | | 4/2012 |
| WO | 2014/160958 A1 | | 10/2014 |
| WO | 2016/151558 A1 | | 9/2016 |
| WO | 2018/075758 A1 | | 4/2018 |
| WO | 2018/075761 A1 | | 4/2018 |

OTHER PUBLICATIONS

Given, A. et al., "Development and validation of an alpha fetoprotein immunoassay using Gyros technology," Journal of Pharmaceutical and Biomedical Analysis, vol. 64-65, May 1, 2012, pp. 8-15.
Haukanes, B-I et al., "Application of Magnetic Beads in Bioassays," Biotechnology. The International Monthly for Industrial Biology, Nature Publishing Group, US, vol. 11 (11):60-63 (1993).
International Preliminary Report on Patentability, PCT/US2017/057377, dated Apr. 29, 2019, 7 pages.
International Search Report and Written Opinion, PCT/US2017/057377, dated Jan. 31, 2019, 11 pages.
Mora, J et al., "Application of the Gyrolab(TM) platform to ligand-binding assays: a user's perspective," Bioanalysis, vol. 2(10):1711-1715 (Oct. 1, 2010).
U.S. Appl. No. 16/342,245, filed Jul. 29, 2019, Mark Dysinger.
Hudlikar, M. et al., "Controlled Multi-functionalization Facilitates Targeted Delivery of Nanoparticles to Cancer Cells," Chemistry, vol. 22(4): 1415-1423 (2016).
International Preliminary Report on Patentability, PCT/US2017/057372, dated Apr. 23, 2019, 9 pages.
International Search Report and Written Opinion, PCT/US2017/057372, dated Mar. 23, 2018, 15 pages.
Scalia, G. et al., "Lifetime of fluorescent dye molecules in dense aqueous suspensions of polystyrene nanoparticles," Opt Express, vol. 23(23):29342-52 (2015).

(Continued)

*Primary Examiner* — Ann Montgomery
(74) *Attorney, Agent, or Firm* — Nelson Mullins Riley & Scarborough LLP; Jane E. Remillard, Esq.; Jill Gorny Sloper, Esq.

(57) ABSTRACT

A method of quantitating free (unbound) human C5a complement protein (C5a) from a sample comprising: binding biotinylated anti-C5a capture antibody to strepavidin-coated particles; capturing the free (unbound) C5 in the sample; detecting the captured free C5a; and quantitating the captured free C5 using laser-induced fluorescence detection; wherein the method is performed in a Gyros Bioaffy 200 CD in a Gyrolab xPlore or a Gyrolab XP instrument; wherein human C5 is first removed from the sample.

16 Claims, 4 Drawing Sheets

Specification includes a Sequence Listing.

(56) References Cited

OTHER PUBLICATIONS

Thermo Scientific et al: "ELISA technical guide and protocols Table of Contents," Jan. 25, 2010, Retrieved from the Internet: URL:https://tools.thermofisher.com/content/sfs/brochures/TR0065-ELISA-guide.pdf [retrieved on Jan. 10, 2018.

Zhang, S et al., "Visualizing Dengue Virus through Alexa Fluor Labeling," JoVE, vol. 53, 4 pages (2011).

Cai, H. et al., "Automation of ELISAs & evaluation of emerging technologies for high throughout quantitation of protein impurities," Pharmaceutical Bioprocessing, vol. 3(7): 427-441 (2015).

Genetic News, New Tools Aim to Reduce Turnaround Times in Biotherapeutic Development and Production, 8 pages (2011).

Given, A. et al., "Development and validation of an alpha fetoprotein immunoassay using Gyros technology," Journal of Pharmaceutical and Biomedical Analysis, vol. 64-65:8-15 (2012).

Heo, J. et al., "A microfluidic approach to high throughput quantification of host cell protein impurities for bioprocess development," Pharm. Bioprocess, vol. 2(2):129-139 (2014).

Leary, B. et al., "Bioanalytical platform comparison using a generic human IgG PK assay format," Journal of Immunological Methods, vol. 397: 28-36 (2013).

Patel, V. et al., "Automating bioanalytical sample analysis through enhanced system integration," Bioanalysis, vol. 5(13):1649-1659 (2013).

Press Release, Gyros Protein Technologies Introduces the Gyrolab xPand New platform aims to improve Immunoassay workflow, flexibility, and speed in biotherapeutic discovery, development, and production UPPSALA, Sweden, Mar. 19, 2018, 2 pages.

* cited by examiner

| Sample | Treatment Ratio, Vol beads:vol Matrix Sample | Free C5a Result, ng/mL | Free C5 Result, µg/mL (ALXN1007 Capture) | Free C5 Result, µg/mL (Eculizumab Capture) |
|---|---|---|---|---|
| 02 | NA | 5.51 | 4.74 | 150.3 |
| 02 Beads | 1:1 | 5.48 | 1.38 | 45.03 |
| 02 Beads 2 | 2:1 | 3.22 | 0.4 | 9.05 |
| 03 | NA | 4.71 | 2.37 | 75.42 |
| 03 Beads | 1:1 | 5.64 | 1.19 | 22.83 |
| 03 Beads 2 | 2:1 | 3.66 | 0.19 | 2.8 |
| 04 | NA | 3.59 | 3.99 | 127.1 |
| 04 Beads | 1:1 | 3.45 | 0.82 | 32.39 |
| 04 Beads 2 | 2:1 | 1.80 | 0.2 | 4.22 |
| 05 | NA | 8.65 | 2.09 | 69.42 |
| 05 Beads | 1:1 | 9.44 | 0.69 | 22.18 |
| 05 Beads 2 | 2:1 | 2.37 | 0.17 | 3.17 |
| 06 | NA | 4.13 | 3.93 | 120.4 |
| 06 Beads | 1:1 | 4.29 | 1.25 | 35.4 |
| 06 Beads 2 | 2:1 | 2.43 | 0.36 | 6.19 |
| 07 | NA | 5.91 | 3.66 | 54.19 |
| 07 Beads | 1:1 | 6.10 | 0.55 | 4.71 |
| 07 Beads 2 | 2:1 | 4.42 | 0.14 | 0.59 |
| 08 | NA | 3.49 | 1.45 | 52.0 |
| 08 Beads | 1:1 | 2.86 | 0.41 | 7.78 |
| 08 Beads 2 | 2:1 | 1.51 | 0.11 | 0.94 |

FIG. 3

| Sample | Treatment Ratio, Vol Beads:vol Matrix Sample | Free C5a Result, ng/mL | Free C5 Result, µg/mL (ALXN1007 Capture) | Free C5 Result, µg/mL (Eculizumab Capture) |
|---|---|---|---|---|
| 02 | NA | 3.54 | 5.11 | 65.8 |
| 02 Beads Rexxip Buffer | 2:1 | 1.84 | 0.68 | 14.1 |
| 02 Beads 1M NaCl 0.5%Tw20 | 2:1 | 1.79 | 0.52 | 12.9 |
| 03 | NA | 3.74 | 4.63 | 61.3 |
| 03 Beads Rexxip Buffer | 2:1 | 2.39 | 0.61 | 9.2 |
| 03 Beads 1M NaCl 0.5%Tw20 | 2:1 | 2.32 | 0.34 | 6.4 |
| 04 | NA | 3.25 | 5.79 | 90.6 |
| 04 Beads Rexxip Buffer | 2:1 | 1.53 | 0.68 | 13.2 |
| 04 Beads 1M NaCl 0.5%Tw20 | 2:1 | 1.26 | 0.37 | 9.5 |
| 05 | NA | 8.37 | 4.04 | 56.2 |
| 05 Beads Rexxip Buffer | 2:1 | 5.29 | 0.35 | 7.9 |
| 05 Beads 1M NaCl 0.5%Tw20 | 2:1 | 5.11 | 0.31 | 6.3 |

FIG. 4

| 1% PMT | Endogenous | Theoretical End + Spike | Actual End + Spike | % Recovery |
|---|---|---|---|---|
| Donor 1 | 5.56 | 10.1 | 6.7 | 66.3 |
| Donor 2 | 5.05 | 9.6 | 8.9 | 92.7 |
| Donor 3 | 5.17 | 9.7 | 9.6 | 99.0 |
| Donor 4 | 6.41 | 10.9 | 9.8 | 89.9 |
| Donor 5 | 2.75 | 7.5 | 6.75 | 90.0 |

| 5% PMT | Endogenous | Theoretical End + Spike | Actual End + Spike | % Recovery |
|---|---|---|---|---|
| Donor 1 | 5.46 | 10.0 | 6.9 | 69.0 |
| Donor 2 | 4.95 | 9.5 | 8.7 | 91.6 |
| Donor 3 | 5.02 | 9.6 | 9.5 | 99.0 |
| Donor 4 | 6.32 | 10.8 | 9.7 | 89.8 |
| Donor 5 | 2.66 | 7.4 | 6.6 | 89.2 |

FIG. 5

SEQUENCE LISTING

<160> NUMBER OF SEQ ID NOS: 18

<210> SEQ ID NO 1
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

```
Leu Ser Ala Ser Val Gly Asp Arg Val Thr Ile Thr Cys Arg Ala Ser
             35                  40                  45

Glu Ser Val Asp Ser Tyr Gly Asn Ser Phe Met His Trp Tyr Gln Gln
 50                  55                  60

Lys Pro Gly Lys Ala Pro Lys Leu Leu Ile Tyr Arg Ala Ser Asn Leu
 65                  70                  75                  80

Glu Ser Gly Val Pro Ser Arg Phe Ser Gly Ser Gly Ser Gly Thr Asp
                 85                  90                  95

Phe Thr Leu Thr Ile Ser Ser Leu Gln Pro Glu Asp Phe Ala Thr Tyr
            100                 105                 110

Tyr Cys Gln Gln Ser Asn Glu Asp Pro Tyr Thr Phe Gly Gly Gly Thr
        115                 120                 125

Lys Val Glu Ile Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
210                 215                 220

Gln Gly Leu Ser Ser Pro Val Thr Lys Ser Phe Asn Arg Gly Glu Cys
225                 230                 235                 240

<210> SEQ ID NO 2
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Met Thr Gln Ser Pro Ser Ser Leu Ser Ala Ser Val Gly
 1               5                  10                  15

Asp Arg Val Thr Ile Thr Cys Arg Ala Ser Glu Ser Val Asp Ser Tyr
             20                  25                  30

Gly Asn Ser Phe Met His Trp Tyr Gln Gln Lys Pro Gly Lys Ala Pro
         35                  40                  45

Lys Leu Leu Ile Tyr Arg Ala Ser Asn Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ser Asn
                 85                  90                  95

Glu Asp Pro Tyr Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160
```

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 3
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 4
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Tyr
            20                  25                  30

Gly Asn Ser Phe Met His Trp Tyr Gln Gln Lys Pro Gly Lys Ala Pro
        35                  40                  45

Lys Leu Leu Ile Tyr Arg Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Tyr Thr Phe Gly Gly Gly Thr Lys Val Glu Ile Lys Arg
            100                 105                 110

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ala Ser Glu Ser Val Asp Ser Tyr Gly Asn Ser Phe Met His
1               5                   10                  15

<210> SEQ ID NO 6
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ala Ser Asn Leu Glu Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Gln Ser Asn Glu Asp Pro Tyr Thr
1               5

<210> SEQ ID NO 8
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 9
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Asp Trp Thr Trp Arg Val Phe Cys Leu Leu Ala Val Ala Pro Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Ser Met Asp Trp Val Arg Gln Ala Pro Gly Gln Gly Leu
    50                  55                  60
```

```
Glu Trp Met Gly Ala Ile His Leu Asn Thr Gly Tyr Thr Asn Tyr Asn
65                  70                  75                  80

Gln Lys Phe Lys Gly Arg Val Thr Met Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Gly Phe Tyr Asp Gly Tyr Ser Pro Met Asp Tyr
        115                 120                 125

Trp Gly Gln Gly Thr Thr Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser Gln Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Gln Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Arg Leu Thr Val Asp Lys
            420                 425                 430

Ser Arg Trp Gln Glu Gly Asn Val Phe Ser Cys Ser Val Met His Glu
        435                 440                 445

Ala Leu His Asn His Tyr Thr Gln Lys Ser Leu Ser Leu Ser Leu Gly
    450                 455                 460

Lys
465
```

<210> SEQ ID NO 10
<211> LENGTH: 446
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ser Met Asp Trp Val Arg Gln Ala Pro Gly Gln Gly Leu Glu Trp Met
        35                  40                  45

Gly Ala Ile His Leu Asn Thr Gly Tyr Thr Asn Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Phe Tyr Asp Gly Tyr Ser Pro Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365
```

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
            405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
            435                 440                 445

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Met Asp Trp Thr Trp Arg Val Phe Cys Leu Leu Ala Val Ala Pro Gly
1               5                   10                  15

Ala His Ser

<210> SEQ ID NO 12
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ser Met Asp Trp Val Arg Gln Ala Pro Gly Gln Gly Leu Glu Trp Met
            35                  40                  45

Gly Ala Ile His Leu Asn Thr Gly Tyr Thr Asn Tyr Asn Gln Lys Phe
        50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Gly Phe Tyr Asp Gly Tyr Ser Pro Met Asp Tyr Trp Gly Gln
            100                 105                 110

Gly Thr Thr Val Thr Val Ser Ser
        115                 120

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Tyr Ser Met Asp

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Ile His Leu Asn Thr Gly Tyr Thr Asn Tyr Asn Gln Lys Phe Lys
1               5                   10                  15

Gly

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Phe Tyr Asp Gly Tyr Ser Pro Met Asp Tyr
1               5                   10

<210> SEQ ID NO 16
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

```
Leu Asn Gly Lys Glu Tyr Lys Cys Lys Val Ser Asn Lys Gly Leu Pro
            195                 200                 205

Ser Ser Ile Glu Lys Thr Ile Ser Lys Ala Lys Gly Gln Pro Arg Glu
            210                 215                 220

Pro Gln Val Tyr Thr Leu Pro Pro Ser Gln Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
            275                 280                 285

Leu Thr Val Asp Lys Ser Arg Trp Gln Glu Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Leu Gly Lys
            325

<210> SEQ ID NO 17
<211> LENGTH: 74
<212> TYPE: PRT
<213> ORGANISM: Homo sapiens

<400> SEQUENCE: 17

Thr Leu Gln Lys Lys Ile Glu Glu Ile Ala Ala Lys Tyr Lys His Ser
1               5                   10                  15

Val Val Lys Lys Cys Cys Tyr Asp Gly Ala Cys Val Asn Asn Asp Glu
            20                  25                  30

Thr Cys Glu Gln Arg Ala Ala Arg Ile Ser Leu Gly Pro Arg Cys Ile
            35                  40                  45

Lys Ala Phe Thr Glu Cys Cys Val Val Ala Ser Gln Leu Arg Ala Asn
        50                  55                  60

Ile Ser His Lys Asp Met Gln Leu Gly Arg
65                  70

<210> SEQ ID NO 18
<211> LENGTH: 73
<212> TYPE: PRT
<213> ORGANISM: Homo sapiens

<400> SEQUENCE: 18

Thr Leu Gln Lys Lys Ile Glu Glu Ile Ala Ala Lys Tyr Lys His Ser
1               5                   10                  15

Val Val Lys Lys Cys Cys Tyr Asp Gly Ala Cys Val Asn Asn Asp Glu
            20                  25                  30

Thr Cys Glu Gln Arg Ala Ala Arg Ile Ser Leu Gly Pro Arg Cys Ile
            35                  40                  45

Lys Ala Phe Thr Glu Cys Cys Val Val Ala Ser Gln Leu Arg Ala Asn
        50                  55                  60

Ile Ser His Lys Asp Met Gln Leu Gly
65                  70
```

METHOD OF QUANTITATING UNBOUND C5A IN A SAMPLE

RELATED APPLICATIONS

This application is a 35 U.S.C. 371 national stage filing of International Application No. PCT/US2017/057377, filed on Oct. 19, 2017, which claims priority from U.S. Provisional Application No. 62/410,028, filed on Oct. 19, 2016. The contents of these applications are incorporated herein by reference in their entireties.

SEQUENCE LISTING

The instant application contains a Sequence Listing which has been submitted electronically in ASCII format and is hereby incorporated by reference in its entirety. Said ASCII copy, created on Apr. 16, 2019, is named AXJ_264US_SEQ and is 22337 bytes in size.

INCORPORATION OF SEQUENCE LISTING

The instant application contains a Sequence Listing, which has been submitted electronically in ASCII format and is hereby incorporated by reference in its entirety. Said ASCII copy, created on Oct. 18, 2017, is named 1900-427PCT_SL.txt and is 22,607 bytes in size.

TECHNICAL FIELD

This invention relates to the field of immunologically related diseases and assays for quantifying free (unbound) drug target.

BACKGROUND

Complement protein C5a is an important component of the alternative complement cascade, and a target of Alexion drug ALXN1007. Proper quantification of this target is essential for a number of reasons, such as monitoring disease state, modeling, dosage selection, and label claims. ALXN1007 has 60 pM affinity for human C5a, but also has 5 nM affinity for human C5. The affinity for C5 is based on neoepitope availability when C5 convertase cleaves C5 into C5a and C5b, and is a function of time. This low level affinity for C5 can have an additive effect on the quantitation of C5a in bioassays because like ALXN1007, there are no secondary antibodies that are specific only for C5a; they bind C5 at a lower affinity as well. If C5 is bound by ALXN1007 when the drug is used as a capture antibody in a ligand binding assay format, a proportion of the protein will be recognized and bound by an anti-C5a antibody, thus leading to over-estimation of that which is truly C5a.

SUMMARY

This disclosure provides a method of quantitating free (unbound) human C5a complement protein (C5a) from a sample comprising:
  a. removing human C5 from the sample; wherein the sample is incubated with C5 specific biotinylated antibody coupled to magnetic beads and wherein the magnetic beads coupled to C5 specific biotinylated antibody bound to human C5 are captured with a magnet;
  b. binding biotinylated anti-C5a capture antibody to strepavidin-coated particles; wherein said biotinylated anti-C5a capture antibody is added by capillary action to a Gyros Bioaffy 200 CD comprising columns with the strepavidin-coated particles; wherein said CD is subjected to centrifugal force inside a Gyrolab xPlore or a Gyrolab XP instrument, thus driving the biotinylated anti-C5a capture antibody to the strepavidin-coated particles in the columns;
  c. capturing the free (unbound) C5a in the sample on the capture antibody; wherein the sample after step a. is added to the CD by capillary action; wherein said CD is subjected to centrifugal force inside the Gyrolab xPlore or a Gyrolab XP instrument, thus driving the sample after step a. to the biotinylated anti-C5a capture antibody bound to the strepavidin-coated particles in the columns;
  d. detecting the captured free C5a; wherein an AlexaFluor labeled anti-C5a detection antibody is added to the CD by capillary action, wherein said anti-C5a detection antibody binds C5a at a different epitope from the epitope bound by the capture antibody; wherein said CD is subjected to centrifugal force inside the Gyrolab xPlore or a Gyrolab XP instrument, thus driving the detection antibody to the free C5a bound to the capture antibody bound to the strepavidin-coated particles in the columns; and
  e. quantitating the captured free C5a using laser-induced fluorescence detection.

Without limiting the disclosure, a number of embodiments of the disclosure are described below for purpose of illustration.

Item 1. A method of quantitating free (unbound) human C5a complement protein (C5a) from a sample comprising:
  a. removing human C5 from the sample; wherein the sample is incubated with C5 specific biotinylated antibody coupled to magnetic beads and wherein the magnetic beads coupled to C5 specific biotinylated antibody bound to human C5 are captured with a magnet;
  b. binding biotinylated anti-C5a capture antibody to strepavidin-coated particles; wherein said biotinylated anti-C5a capture antibody is added by capillary action to a Gyros Bioaffy 200 CD comprising columns with the strepavidin-coated particles; wherein said CD is subjected to centrifugal force inside a Gyrolab xPlore or a Gyrolab XP instrument, thus driving the biotinylated anti-C5a capture antibody to the strepavidin-coated particles in the columns;
  c. capturing the free (unbound) C5a in the sample on the capture antibody; wherein the sample after step a. is added to the CD by capillary action; wherein said CD is subjected to centrifugal force inside the Gyrolab xPlore or a Gyrolab XP instrument, thus driving the sample after step a. to the biotinylated anti-C5a capture antibody bound to the strepavidin-coated particles in the columns;
  d. detecting the captured free C5a; wherein an AlexaFluor labeled anti-C5a detection antibody is added to the CD by capillary action, wherein said anti-C5a detection antibody binds C5a at a different epitope from the epitope bound by the capture antibody; wherein said CD is subjected to centrifugal force inside the Gyrolab xPlore or a Gyrolab XP instrument, thus driving the detection antibody to the free C5a bound to the capture antibody bound to the strepavidin-coated particles in the columns; and
  e. quantitating the captured free C5a using laser-induced fluorescence detection.

Item 2. The method of item 1, further comprising calculating the concentration or amount of free C5a antibody by comparing the value obtained from step c. to a standard curve prepared from known amounts of C5a added to a C5a depleted sample using method of claim 1 (at least steps b.-e.; and optionally step a.).

Item 3. The method of item 1 or item 2, further comprising calculating the concentration of free C5 antibody with the Gyros Evaluator software.

Item 4. The method of any one of the preceding items, wherein the sample is obtained from a human patient.

Item 5. The method of item 4, wherein said sample is a serum sample.

Item 6. The method of any one of the preceding items, wherein the patient has been treated with an anti-C5a antibody.

Item 7. The method of claim 6, wherein the patient has been treated with ALXN1007.

Item 8. The method of any one of the preceding items, wherein the magnetic beads are Dynabead magnetic beads.

Item 9. The method of any one of the preceding items, wherein the C5 specific antibody is biotinylated N19/8.

Item 10. The method of any one of the preceding items, wherein the biotinylated capture antibody is ALXN1007.

Item 11. The method of any one of the preceding items, wherein the anti-C5a detection antibody is clone 2942.

Item 12. The method of any one of the preceding items, wherein Rexxip AN buffer or 1M NaCl/0.5% Tween 20 buffer is used for diluting samples and Rexxip F buffer is used for diluting the detection antibody.

Item 13. The method of anyone of the preceding items, further comprising priming the Gyros instrument is two separate times with Bioaffy wash 1 and pH 11 buffer.

Numerous other aspects are provided in accordance with these and other aspects of the invention. Other features and aspects of the present invention will become more fully apparent from the following detailed description and the appended claims.

BRIEF DESCRIPTION OF THE DRAWINGS

FIG. 3 shows bead effect on C5a and C5.

FIG. 4 shows Bead Effect—Rexxip AN vs 1M NaCl/0.5% Tween 20.

FIG. 5 shows free C5a early bead treatment selectivity.

DETAILED DESCRIPTION

Figure 1:
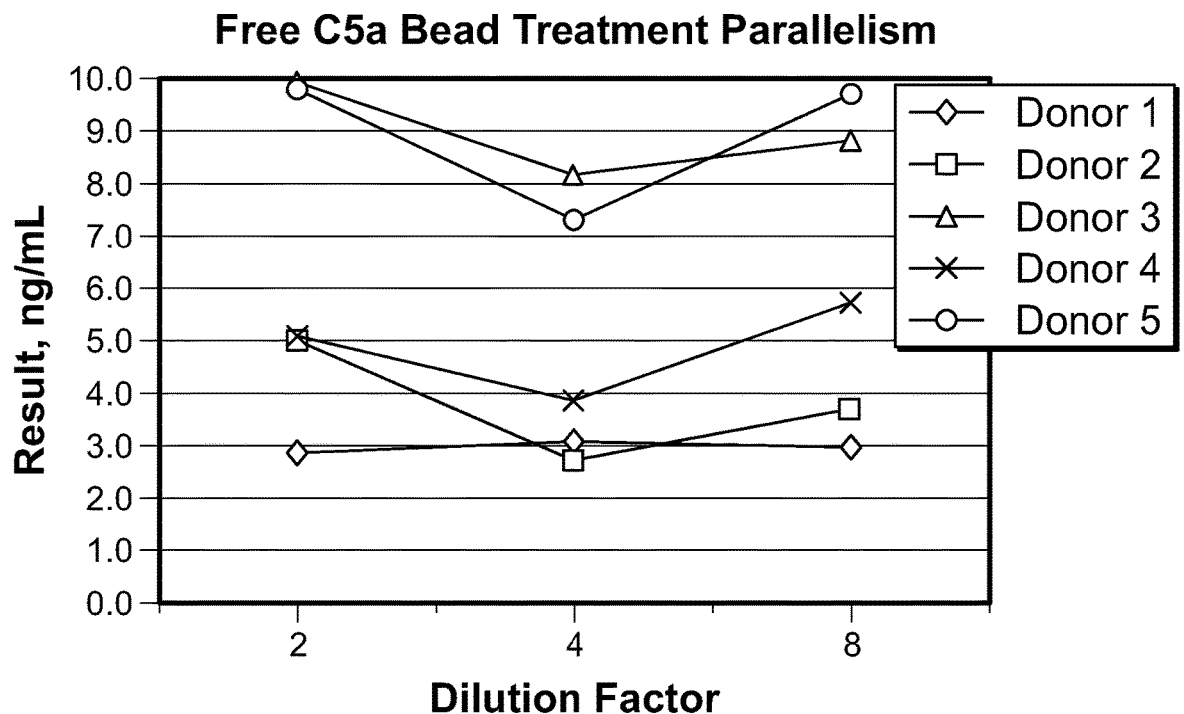
FIG. 1 is a graph showing free C5a bead treatment parallelism.

As used herein, the word "a" or "plurality" before a noun represents one or more of the particular noun. For example, the phrase "a mammalian cell" represents "one or more mammalian cells."

The term "mammalian cell" is known in the art and can refer to any cell from or derived from any mammal including, for example, a human, a hamster, a mouse, a green monkey, a rat, a pig, a cow, a hamster, or a rabbit. In some embodiments, the mammalian cell can be an immortalized cell, a differentiated cell, an undifferentiated cell, a stem cell, etc.

As used herein, the terms "subject" and "patient" are used interchangeably. A patient or a subject can be a human patient or a human subject.

The term "recombinant protein" is known in the art. Briefly, the term "recombinant protein" can refer to a protein that can be manufactured using a cell culture system. The cells in the cell culture system can be derived from, for example, a mammalian cell, including a human cell, an insect cell, a yeast cell, or a bacterial cell. In general, the cells in the cell culture contain an introduced nucleic acid encoding the recombinant protein of interest (which nucleic acid can be borne on a vector, such as a plasmid vector). The nucleic acid encoding the recombinant protein can also contain a heterologous promoter operably linked to a nucleic acid encoding the protein.

The term "immunoglobulin" is known in the art. Briefly, the term "immunoglobulin" can refer to a polypeptide containing an amino acid sequence of at least 15 amino acids (e.g., at least 20, 30, 40, 50, 60, 70, 80, 90, or 100 amino acids, or more than 100 amino acids) of an immunoglobulin protein (e.g., a variable domain sequence, a framework sequence, or a constant domain sequence). The immunoglobulin can, for example, include at least 15 amino acids of a light chain immunoglobulin, e.g., at least 15 amino acids of a heavy chain immunoglobulin, such as a CDRH3. The immunoglobulin may be an isolated antibody (e.g., an IgG, IgE, IgD, IgA, or IgM). The immunoglobulin may be a subclass of IgG (e.g., IgG1, IgG2, IgG3, or IgG4). The immunoglobulin can be an antibody fragment, e.g., a Fab fragment, a F(ab')$_2$ fragment, or a scFv. The immunoglobulin can also be an engineered protein containing at least one immunoglobulin domain (e.g., a fusion protein). The engineered protein or immunoglobulin-like protein can also be a bi-specific antibody or a tri-specific antibody, or a dimer, trimer, or multimer antibody, or a diabody, a DVD-Ig, a CODV-Ig, an Affibody®, or a Nanobody®. Non-limiting examples of immunoglobulins are described herein and additional examples of immunoglobulins are known in the art.

The term "engineered protein" is known in the art. Briefly, the term "engineered protein" can refer to a polypeptide that is not naturally encoded by an endogenous nucleic acid present within an organism (e.g., a mammal). Examples of engineered proteins include modified enzymes with one or more amino acid substitutions, deletions, insertions, or additions that result in an increase in stability and/or catalytic activity of the engineered enzyme, fusion proteins, humanized antibodies, chimeric antibodies, divalent antibodies, trivalent antibodies, four binding domain antibodies, a diabody, and antigen-binding proteins that contain at least one recombinant scaffolding sequence.

The terms "polypeptide," "peptide," and "protein" are used interchangeably and are known in the art and can mean any peptide-bond linked chain of amino acids, regardless of length or post-translational modification.

The term "antibody" is known in the art. The term "antibody" may be used interchangeably with the term "immunoglobulin." Briefly, it may refer to a whole antibody comprising two light chain polypeptides and two heavy chain polypeptides. Whole antibodies include different antibody isotypes including IgM, IgG, IgA, IgD, and IgE antibodies. The term "antibody" includes, for example, a polyclonal antibody, a monoclonal antibody, a chimerized or chimeric antibody, a humanized antibody, a primatized antibody, a deimmunized antibody, and a fully human antibody. The antibody can be made in or derived from any of a variety of species, e.g., mammals such as humans, non-human primates (e.g., orangutan, baboons, or chimpanzees), horses, cattle, pigs, sheep, goats, dogs, cats, rabbits, guinea pigs, gerbils, hamsters, rats, and mice. The antibody can be a purified or a recombinant antibody.

The antibody can also be an engineered protein or antibody-like protein containing at least one immunoglobulin domain (e.g., a fusion protein). The engineered protein or antibody-like protein can also be a bi-specific antibody or a tri-specific antibody, or a dimer, trimer, or multimer antibody, or a diabody, a DVD-Ig, a CODV-Ig, an Affibody®, or a Nanobody®.

The term "antibody fragment," "antigen-binding fragment," or similar terms are known in the art and can, for example, refer to a fragment of an antibody that retains the ability to bind to a target antigen (e.g., human C5) and inhibit the activity of the target antigen. Such fragments include, e.g., a single chain antibody, a single chain Fv fragment (scFv), an Fd fragment, a Fab fragment, a Fab' fragment, or an F(ab')2 fragment. A scFv fragment is a single polypeptide chain that includes both the heavy and light chain variable regions of the antibody from which the scFv is derived. In addition, intrabodies, minibodies, triabodies, and diabodies are also included in the definition of antibody and are compatible for use in the methods described herein. See, e.g., Todorovska et al. (2001) *J Immunol Methods* 248(1):47-66; Hudson and Kortt (1999) *J Immunol Methods* 231(1):177-189; Poljak (1994) *Structure* 2(12):1121-1123; Rondon and Marasco (1997) *Annual Review of Microbiology* 51:257-283. An antigen-binding fragment can also include the variable region of a heavy chain polypeptide and the variable region of a light chain polypeptide. An antigen-binding fragment can thus comprise the CDRs of the light chain and heavy chain polypeptide of an antibody.

The term "antibody fragment" also can include, e.g., single domain antibodies such as camelized single domain antibodies. See, e.g., Muyldermans et al. (2001) *Trends Biochem Sci* 26:230-235; Nuttall et al. (2000) *Curr Pharm Biotech* 1:253-263; Reichmann et al. (1999) *J Immunol Meth* 231:25-38; PCT application publication nos. WO 94/04678 and WO 94/25591; and U.S. Pat. No. 6,005,079. The term "antibody fragment" also includes single domain antibodies comprising two $V_H$ domains with modifications such that single domain antibodies are formed.

The term "antibody" also includes "antigen-binding fragment" and "antibody fragment."

The term "$k_a$" is well known in the art and can refer to the rate constant for association of an antibody to an antigen. The term "$k_d$" is also well known in the art and can refer to the rate constant for dissociation of an antibody from the antibody/antigen complex. And the term "$K_D$" is known in the art and can refer to the equilibrium dissociation constant of an antibody-antigen interaction. The equilibrium dissociation constant is deduced from the ratio of the kinetic rate constants, $K_D=k_d/k_a$. Such determinations are typically measured at, for example, 25° C. or 37° C. For example, the kinetics of antibody binding to human C5 can be determined at pH 8.0, 7.4, 7.0, 6.5 and 6.0 via surface plasmon resonance ("SPR") on a BIAcore 3000 instrument using an anti-Fc capture method to immobilize the antibody.

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about," whether or not the term is explicitly used, unless explicitly stated otherwise. As used herein, the singular forms "a," "an," and "the" include plural referents unless the context clearly dictates otherwise.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The Complement System

As is well known, the complement system acts in conjunction with other immunological systems of the body to defend against intrusion of cellular and viral pathogens. There are at least 25 complement proteins. Complement components achieve their immune defensive functions by interacting in a series of intricate but precise enzymatic cleavage and membrane binding events. The resulting complement cascade leads to the production of products with opsonic, immunoregulatory, and lytic functions.

The complement cascade can progress via the classical pathway ("CP"), the lectin pathway ("LP"), or the alternative pathway ("AP"). The lectin pathway is typically initiated with binding of mannose-binding lectin ("MBL") to high mannose substrates. The AP can be antibody independent, and can be initiated by certain molecules on pathogen surfaces. The CP is typically initiated by antibody recognition of, and binding to, an antigenic site on a target cell. These pathways converge at the C3 convertase—the point where complement component C3 is cleaved by an active protease to yield C3a and C3b.

The AP C3 convertase is initiated by the spontaneous hydrolysis of complement component C3, which is abundant in the plasma in the blood. This process, also known as "tickover," occurs through the spontaneous cleavage of a thioester bond in C3 to form C3i or C3 ($H_2O$). Tickover is facilitated by the presence of surfaces that support the binding of activated C3 and/or have neutral or positive charge characteristics (e.g., bacterial cell surfaces). This formation of C3($H_2O$) allows for the binding of plasma protein Factor B, which in turn allows Factor D to cleave Factor B into Ba and Bb. The Bb fragment remains bound to C3 to form a complex containing C3 ($H_2O$)Bb—the "fluid-phase" or "initiation" C3 convertase. Although only produced in small amounts, the fluid-phase C3 convertase can cleave multiple C3 proteins into C3a and C3b and results in the generation of C3b and its subsequent covalent binding to a surface (e.g., a bacterial surface). Factor B bound to the surface-bound C3b is cleaved by Factor D to thus form the surface-bound AP C3 convertase complex containing C3b, Bb. See, e.g., Müller-Eberhard (1988) *Ann Rev Biochem* 57:321-347.

The AP C5 convertase—$(C3b)_2$,Bb—is formed upon addition of a second C3b monomer to the AP C3 convertase. See, e.g., Medicus et al. (1976) *J Exp Med* 144:1076-1093 and Fearon et al. (1975) *J Exp Med* 142:856-863. The role of the second C3b molecule is to bind C5 and present it for cleavage by Bb. See, e.g., Isenman et al. (1980) *J Immunol* 124:326-331. The AP C3 and C5 convertases are stabilized by the addition of the trimeric protein properdin as described in, e.g., Medicus et al. (1976), supra. However, properdin binding is not required to form a functioning alternative pathway C3 or C5 convertase. See, e.g., Schreiber et al. (1978) *Proc Natl Acad Sci USA* 75: 3948-3952, and Sissons et al. (1980) *Proc Natl Acad Sci USA* 77: 559-562.

The CP C3 convertase is formed upon interaction of complement component C1, which is a complex of C1q, C1r, and C1s, with an antibody that is bound to a target antigen (e.g., a microbial antigen). The binding of the C1q portion of C1 to the antibody-antigen complex causes a conformational change in C1 that activates C1r. Active C1r then cleaves the C1-associated C1s to thereby generate an active serine protease. Active C1s cleaves complement component C4 into C4b and C4a. Like C3b, the newly generated C4b fragment contains a highly reactive thiol that readily forms amide or ester bonds with suitable molecules on a target surface (e.g., a microbial cell surface). C1s also cleaves complement component C2 into C2b and C2a. The complex formed by C4b and C2a is the CP C3 convertase, which is capable of processing C3 into C3a and C3b. The CP C5 convertase—C4b,C2a,C3b—is formed upon addition of a C3b monomer to the CP C3 convertase. See, e.g., Müller-Eberhard (1988), supra and Cooper et al. (1970) *J Exp Med* 132:775-793.

In addition to its role in C3 and C5 convertases, C3b also functions as an opsonin through its interaction with complement receptors present on the surfaces of antigen-presenting cells such as macrophages and dendritic cells. The opsonic function of C3b is generally considered to be one of the most important anti-infective functions of the complement system. Patients with genetic lesions that block C3b function are prone to infection by a broad variety of pathogenic organisms, while patients with lesions later in the complement cascade sequence, i.e., patients with lesions that block C5 functions, are found to be more prone only to Neisseria infection, and then only somewhat more prone.

The AP and CP C5 convertases cleave C5, which is a 190 kDa beta globulin found in normal human serum at approximately 75 µg/ml (0.4 µM). C5 is glycosylated, with about 1.5-3 percent of its mass attributed to carbohydrate. Mature C5 is a heterodimer of a 999 amino acid 115 kDa alpha chain that is disulfide linked to a 655 amino acid 75 kDa beta chain. C5 is synthesized as a single chain precursor protein product of a single copy gene (Haviland et al. (1991) *J Immunol.* 146:362-368). The cDNA sequence of the transcript of this human gene predicts a secreted pro-C5 precursor of 1658 amino acids along with an 18 amino acid leader sequence. See, e.g., U.S. Pat. No. 6,355,245.

The pro-C5 precursor is cleaved after amino acids 655 and 659, to yield the beta chain as an amino terminal fragment (amino acid residues +1 to 655 of the above sequence) and the alpha chain as a carboxyl terminal fragment (amino acid residues 660 to 1658 of the above sequence), with four amino acids (amino acid residues 656-659 of the above sequence) deleted between the two.

C5a is cleaved from the alpha chain of C5 by either alternative or classical C5 convertase as an amino terminal fragment comprising the first 74 amino acids of the alpha chain (i.e., amino acid residues 660-733 of the above sequence). Approximately 20 percent of the 11 kDa mass of C5a is attributed to carbohydrate. The cleavage site for convertase action is at, or immediately adjacent to, amino acid residue 733. A compound that would bind at, or adjacent to, this cleavage site would have the potential to block access of the C5 convertase enzymes to the cleavage site and thereby act as a complement inhibitor. A compound that binds to C5 at a site distal to the cleavage site could also have the potential to block C5 cleavage, for example, by way of steric hindrance-mediated inhibition of the interaction between C5 and the C5 convertase. A compound, in a mechanism of action consistent with that of the tick saliva complement inhibitor, Ornithodoros moubata C inhibitor ('OmCI'), may also prevent C5 cleavage by reducing flexibility of the C345C domain of the alpha chain of C5, which reduces access of the C5 convertase to the cleavage site of C5. See, e.g., Fredslund et al. (2008) *Nat Immunol* 9(7): 753-760.

C5 can also be activated by means other than C5 convertase activity. Limited trypsin digestion (see, e.g., Minta and Man (1997) *J Immunol* 119:1597-1602 and Wetsel and Kolb (1982) *J Immunol* 128:2209-2216) and acid treatment (Yamamoto and Gewurz (1978) *J Immunol* 120:2008 and Damerau et al. (1989) *Molec Immunol* 26:1133-1142) can also cleave C5 and produce active C5b.

Cleavage of C5 releases C5a, a potent anaphylatoxin and chemotactic factor, and leads to the formation of the lytic terminal complement complex, C5b-9. C5a and C5b-9 also have pleiotropic cell activating properties, by amplifying the release of downstream inflammatory factors, such as hydrolytic enzymes, reactive oxygen species, arachidonic acid metabolites and various cytokines.

The first step in the formation of the terminal complement complex involves the combination of C5b with C6, C7, and C8 to form the C5b-8 complex at the surface of the target cell. Upon the binding of the C5b-8 complex with several C9 molecules, the membrane attack complex ("MAC", C5b-9, terminal complement complex—"TCC") is formed. When sufficient numbers of MACs insert into target cell membranes the openings they create (MAC pores) mediate rapid osmotic lysis of the target cells, such as red blood cells. Lower, non-lytic concentrations of MACs can produce other effects. In particular, membrane insertion of small numbers of the C5b-9 complexes into endothelial cells and platelets can cause deleterious cell activation. In some cases, activation may precede cell lysis.

C3a and C5a are anaphylatoxins. These activated complement components can trigger mast cell degranulation, which releases histamine from basophils and mast cells, and other mediators of inflammation, resulting in smooth muscle contraction, increased vascular permeability, leukocyte activation, and other inflammatory phenomena including cellular proliferation resulting in hypercellularity. C5a also functions as a chemotactic peptide that serves to attract pro-inflammatory granulocytes to the site of complement activation.

C5a receptors are found on the surfaces of bronchial and alveolar epithelial cells and bronchial smooth muscle cells. C5a receptors have also been found on eosinophils, mast cells, monocytes, neutrophils, and activated lymphocytes.

While a properly functioning complement system provides a robust defense against infecting microbes, inappropriate regulation or activation of complement has been implicated in the pathogenesis of a variety of disorders, including, e.g., rheumatoid arthritis; lupus nephritis; asthma; ischemia-reperfusion injury; atypical hemolytic uremic syndrome ("aHUS"); dense deposit disease; paroxysmal nocturnal hemoglobinuria (PNH); macular degeneration (e.g., age-related macular degeneration; hemolysis, elevated liver enzymes, and low platelets (HELLP) syndrome; thrombotic thrombocytopenic purpura (TTP); spontaneous fetal loss; Pauci-immune vasculitis; epidermolysis bullosa; recurrent fetal loss; multiple sclerosis (MS); traumatic brain injury; and injury resulting from myocardial infarction, cardiopulmonary bypass and hemodialysis. See, e.g., Holers et al. (2008) *Immunological Reviews* 223:300-316.

As used herein, the term "C5a" refers to a protein fragment released from cleavage of human complement component C5 by protease C5-convertase into C5a and C5b fragments. The proform of human C5, a 1676 amino acid residue precursor protein, is processed by a series of proteolytic cleavage events. The first 18 peptides (numbered −18 to −1) constitute a signal peptide that is cleaved from the precursor protein. The remaining 1658 amino acid protein is cleaved in two places to form the alpha and beta chains. The first cleavage event occurs between amino acid residues 655 and 656. The second cleavage occurs between amino acid residues 659 and 660. The two cleavage events result in the formation of three distinct polypeptide fragments: (i) a fragment comprising amino acids 1 to 655, which is referred to as the beta chain; (ii) a fragment comprising amino acids 660 to 1658, which is referred to as the alpha chain; and (iii) a tetrapeptide fragment consisting of amino acids 656 to 659. The alpha chain and the beta chain polypeptide fragments are connected to each other via disulfide bond and constitute the mature C5 protein. The CP or AP C5 convertase activates mature C5 by cleaving the alpha chain between residues 733 and 734, which results in the liberation of C5a fragment (amino acids 660 to 733). The remaining portion of mature C5 is fragment C5b, which contains the residues 734 to 1658 of the alpha chain disulfide bonded to the beta chain. In vivo, C5a is rapidly metabolized by a serum enzyme, carboxypeptidase B, to a 73 amino acid form termed "C5a desarg," which has lost the carboxyl terminal arginine residue.

Anti-C5a Antibody

Anti-C5a antibodies (or $V_H/V_L$ domains derived therefrom) suitable for use in the methods disclosed herein can be generated using methods well known in the art. Alternatively, art recognized anti-C5a antibodies can be used. Antibodies that compete with any of these art-recognized antibodies for binding to C5a also can be used.

An exemplary anti-C5a antibody is BNJ383 (also known as "ALXN1007") comprising heavy and light chains having the sequences shown in SEQ ID NOs: 10 and 2, respectively, or antigen binding fragments and variants thereof. BNJ383 is described in International Patent Application Publication No. WO 2011/137395 (e.g., Table 2) and U.S. Pat. No. 9,011,852, the teachings or which are hereby incorporated by reference. BNJ383 is a recombinant humanized monoclonal antibody that binds to complement component C5a and its metabolite C5a desArg. In vitro and in vivo non-clinical data and data from ongoing Phase 1 clinical studies have demonstrated that BNJ383 is well tolerated, is highly specific for its epitope, is a potent antagonist of C5a-mediated signaling and depletes C5a/C5a desArg from the circulation.

In other embodiments, the antibody comprises the heavy and light chain CDRs or variable regions of BNJ383. In one embodiment, the antibody comprises the CDR1, CDR2, and CDR3 domains of the $V_H$ region of BNJ383 having the sequence set forth in SEQ ID NO: 12, and the CDR1, CDR2 and CDR3 domains of the VL region of BNJ383 having the sequence set forth in SEQ ID NO: 4. In another embodiment, the antibody comprises heavy chain CDR1, CDR2 and CDR3 domains having the sequences set forth in SEQ ID NOs: 13, 14, and 15, respectively, and light chain CDR1, CDR2 and CDR3 domains having the sequences set forth in SEQ ID NOs: 5, 6, and 7, respectively. In another embodiment, the antibody comprises a $V_H$ region having the amino acid sequences set forth in SEQ ID NO: 12. In another embodiment, the antibody comprises a $V_L$ region having the amino acid sequences set forth in SEQ ID NO: 4. In another embodiment, the antibody comprises VH and VL regions having the amino acid sequences set forth in SEQ ID NO: 12 and SEQ ID NO: 4, respectively.

The exact boundaries of CDRs have been defined differently according to different methods. In some embodiments, the positions of the CDRs or framework regions within a light or heavy chain variable domain can be as defined by Kabat et al. [(1991) "Sequences of Proteins of Immunological Interest." NIH Publication No. 91-3242, U.S. Department of Health and Human Services, Bethesda, MD]. In such cases, the CDRs can be referred to as "Kabat CDRs" (e.g., "Kabat LCDR2" or "Kabat HCDR1"). In some embodiments, the positions of the CDRs of a light or heavy chain variable region can be as defined by Chothia et al. (1989) Nature 342:877-883. Accordingly, these regions can be referred to as "Chothia CDRs" (e.g., "Chothia LCDR2" or "Chothia HCDR3"). In some embodiments, the positions of the CDRs of the light and heavy chain variable regions can be as defined by a Kabat-Chothia combined definition. In such embodiments, these regions can be referred to as "combined Kabat-Chothia CDRs". Thomas et al. [(1996) Mol Immunol 33(17/18):1389-1401] exemplifies the identification of CDR boundaries according to Kabat and Chothia definitions.

Methods for determining whether an antibody binds to a protein antigen and/or the affinity for an antibody to a protein antigen are known in the art. For example, the binding of an antibody to a protein antigen can be detected and/or quantified using a variety of techniques such as, but not limited to, Western blot, dot blot, surface plasmon resonance (SPR) method (e.g., BIAcore system; Pharmacia Biosensor AB, Uppsala, Sweden and Piscataway, N.J.), or enzyme-linked immunosorbent assay (ELISA). See, e.g., Benny K. C. Lo (2004) "Antibody Engineering: Methods and Protocols," Humana Press (ISBN: 1588290921); Johne et al. (1993) J Immunol Meth 160:191-198; Jonsson et al. (1993) Ann Biol Clin 51:19-26; and Jonsson et al. (1991) Biotechniques 11:620-627.

In one embodiment, the anti-C5a antibody, or antigen binding fragment thereof, binds to a mammalian (e.g., human) C5a protein. For example, the anti-C5a antibody, or antigen binding fragment thereof, can bind to a human C5a protein having the following amino acid sequence: TLQKKIEEIAAKYKHSVVKKCCYDGACVNNDETCEQRAARISLGPRCIKAFTECCVVASQLRANISHKDMQLGR (SEQ ID NO:17). In another embodiment, the anti-C5a antibody, or antigen binding fragment thereof, binds to a desarginated human C5a protein having the following amino acid sequence: TLQKKIEEIAAKYKHSVVKKCCYDGACVNNDETCEQRAARISLGPRCIKAFTECCVVASQLRANISHKDM QLG (SEQ ID NO:18). An anti-C5a antibody, or antigen binding fragment thereof, described herein can bind to both full-length human C5a and desarginated human C5a.

In one embodiment, the anti-C5a antibody, or antigen binding fragment thereof, binds to free human C5a (hC5a; e.g., a human C5a protein comprising, or consisting of, the amino acid sequence depicted in SEQ ID NO:17). In another embodiment, the anti-C5a antibody, or antigen binding fragment thereof, binds to a desarginated form of free C5a, e.g., the desarginated form of human C5a comprising, or consisting of, the amino acid sequence depicted in SEQ ID NO:18. The antibody can bind to a neoepitope of free C5a, which epitope is not present on uncleaved C5 or is present on only a minor fraction of total uncleaved C5.

In one embodiment, the antibody competes for binding with, and/or binds to the same epitope on C5a as, the antibodies described herein. The term "binds to the same epitope" with reference to two or more antibodies means that the antibodies bind to the same segment of amino acid residues, as determined by a given method. Techniques for determining whether antibodies bind to the "same epitope on C5a" with the antibodies described herein include, for example, epitope mapping methods, such as, x-ray analyses of crystals of antigen:antibody complexes which provides atomic resolution of the epitope and hydrogen/deuterium exchange mass spectrometry (HDX-MS). Other methods monitor the binding of the antibody to peptide antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. Antibodies having the same $V_H$ and $V_L$ or the same CDR1, 2 and 3 sequences are expected to bind to the same epitope.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, may be determined using known competition experiments. In certain embodiments, an antibody competes with, and inhibits binding of another antibody to a target by at least 10%, 20%, 30%, 40%, 50%, 60%, 70%, 80%, 90% or 100%. The level of inhibition or competition may be different depending on which antibody is the "blocking antibody" (i.e., the cold antibody that is incubated first with the target). Competing antibodies bind to the same epitope, an overlapping epitope or to adjacent epitopes (e.g., as evidenced by steric hindrance).

Anti-C5a antibodies, or antigen-binding fragments thereof described herein, used in the methods described herein can be generated using a variety of art-recognized techniques.

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, *Eur. J. Immunol.* 6: 511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., *Science* 246: 1275-1281 (1989).

An anti-C5a antibody may be a monoclonal antibody, a chimerized antibody, a humanized antibody, a human antibody, a single chain antibody, a bispecific antibody, etc. An anti-C5a antibody may be a fusion protein. The fusion protein can be constructed recombinantly such that the fusion protein is expressed from a nucleic acid that encodes the fusion protein. The fusion protein can comprise one or more C5a-binding polypeptide segments.

In some embodiments, the anti-C5 antibodies are fused to a targeting moiety. For example, a construct can contain a C5-binding polypeptide and a targeting moiety that targets the polypeptide to a site of complement activation. Such targeting moieties can include, e.g., soluble form of complement receptor 1 (CR1), a soluble form of complement receptor 2 (CR2), or an antibody (or antigen-binding fragment thereof) that binds to C3b and/or C3d.

Methods for generating fusion proteins (e.g., fusion proteins containing a C5a-binding polypeptide and a soluble form of human CR1 or human CR2), including recombinant DNA technology, are known in the art and described in, e.g., U.S. Pat. No. 6,897,290; U.S. patent application publication no. 2005265995; and Song et al. (2003) *J Clin Invest* 11(12):1875-1885.

In certain embodiments, the anti-C5a antibody is a bispecific antibody. Methods for producing a bispecific antibody (e.g., a bispecific antibody comprising an anti-C5a antibody and an antibody that binds to C3b and/or C3d) are also known in the art. A bispecific antibody comprising a C5-binding antibody and any other antibody is contemplated.

A wide variety of bispecific antibody formats are known in the art of antibody engineering and methods for making the bispecific antibodies (e.g., a bispecific antibody comprising an anti-C5a antibody [i.e., a C5a-binding antibody] and an antibody that binds to C3b, C3d, or a tissue-specific antigen) are well within the purview of those skilled in the art. See, e.g., Suresh et al. (1986) *Methods in Enzymology* 121:210; PCT Publication No. WO 96/27011.

Bispecific antibodies also include cross-linked or heteroconjugate antibodies. Heteroconjugate antibodies may be made using any convenient cross-linking methods. Suitable cross-linking agents are well known in the art, and are disclosed in U.S. Pat. No. 4,676,980, along with a number of cross-linking techniques. U.S. Pat. No. 5,534,254 describes several different types of bispecific antibodies including, e.g., single chain Fv fragments linked together by peptide couplers, chelating agents, or chemical or disulfide couplings. In another example, Segal and Bast [(1995) *Curr Protocols Immunol Suppl.* 14:2.13.1-2.13.16] describes methods for chemically cross-linking two monospecific antibodies to thus form a bispecific antibody. A bispecific antibody can be formed, e.g., by conjugating two single chain antibodies which are selected from, e.g., a C5-binding antibody and an antibody that binds to, e.g., C3b, C3d, or a lung-specific antigen, an eye-specific antigen, a kidney-specific antigen, etc.

The bispecific antibody can be a tandem single chain (sc) Fv fragment, which contains two different scFv fragments covalently tethered together by a linker (e.g., a polypeptide linker). See, e.g., Ren-Heidenreich et al. (2004) *Cancer* 100:1095-1103 and Korn et al. (2004) *J Gene Med* 6:642-651.

A bispecific antibody can also be a diabody. Diabody technology described by, e.g., Hollinger et al. (1993) *Proc Natl Acad Sci USA* 90:6444-6448 has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. See also Zhu et al. (1996) *Biotechnology* 14:192-196 and Helfrich et al. (1998) *Int J Cancer* 76:232-239. Bispecific single chain diabodies ("scDb") as well as methods for generating scDb are described in, e.g., Brüsselbach et al. (1999) *Tumor Targeting* 4:115-123; Kipriyanov et al. (1999) *J Mol Biol* 293:41-56; and Nettlebeck et al. (2001) *Mol Ther* 3:882-891.

Variant forms of bispecific antibodies such as the tetravalent dual variable domain immunoglobulin (DVD-Ig) molecules described in Wu et al. (2007) *Nat Biotechnol* 25(11): 1290-1297 can also be used in the methods of this invention.

The DVD-Ig molecules are designed such that two different light chain variable domains ($V_L$) from two different parent antibodies are linked in tandem directly or via a short linker by recombinant DNA techniques, followed by the light chain constant domain. Methods for generating DVD-Ig molecules from two parent antibodies are further described in, e.g., PCT Publication Nos. WO 08/024188 and WO 07/024715. Also embraced is the bispecific format described in, e.g., U.S. patent application publication no. 20070004909. Another bispecific format that can be used is the Cross-Over Dual V Region (CODV-Ig) which is a format for engineering four domain antibody-like molecules described in WO2012/135345. CODV-Ig was shown to be useful in engineering bispecific antibody-like molecules where steric hindrance at the C-terminal V domains (internal) may prevent construction of a DVD-Ig.

The C5a-binding antibodies and/or targeting-moieties that are used to form the bispecific antibody molecules can be, e.g., chimeric, humanized, rehumanized, deimmunized, or fully human, all of which are well known in the art.

An anti-C5a antibody may be produced by recombinant DNA techniques. For example, a nucleic acid encoding a C5a-binding polypeptide can be inserted into an expression vector that contains transcriptional and translational regulatory sequences, which include, e.g., promoter sequences, ribosomal binding sites, transcriptional start and stop sequences, translational start and stop sequences, transcription terminator signals, polyadenylation signals, and enhancer or activator sequences. The regulatory sequences include a promoter and transcriptional start and stop sequences. In addition, the expression vector can include more than one replication system such that it can be maintained in two different organisms, for example in mammalian or insect cells for expression and in a prokaryotic host for cloning and amplification.

Several possible vector systems (such as plasmid vector systems) well known in the art are available for the expression of an anti-C5 antibody from nucleic acids in a number of cells, including in mammalian cells.

The expression vectors can be introduced by methods well known in the art into cells in a manner suitable for subsequent expression of the nucleic acid.

An anti-C5a antibody may be expressed in any appropriate host cells. Appropriate host cells include, for example, yeast, bacteria, insect, plant, and mammalian cells, including bacteria such as *E. coli*, fungi such as *Saccharomyces cerevisiae* and *Pichia pastoris*, insect cells such as SF9, mammalian cell lines (e.g., human cell lines), primary cell lines (e.g., primary mammalian cells), Chinese hamster ovary ("CHO") cells, and a suitable myeloma cell line such as NSO.

In some embodiments, an anti-C5a antibody may be expressed in, and purified from, transgenic animals (e.g., transgenic mammals). For example, an anti-C5a antibody may be produced in transgenic non-human mammals (e.g., rodents, sheep or goats) and isolated from milk as described in, e.g., Houdebine (2002) *Curr Opin Biotechnol* 13(6):625-629; van Kuik-Romeijn et al. (2000) *Transgenic Res* 9(2):155-159; and Pollock et al. (1999) *J Immunol Methods* 231(1-2):147-157.

The anti-C5a antibody may be produced from cells by culturing a host cell transformed with the expression vector containing nucleic acid encoding the polypeptides, under conditions, and for an amount of time, sufficient to allow expression of the proteins. Such conditions for protein expression will vary with the choice of the expression vector and the host cell, and will be easily ascertained by one skilled in the art through routine experimentation. See, e.g., Current Protocols in Molecular Biology, Wiley & Sons, and Molecular Cloning—A Laboratory Manual—3rd Ed., Cold Spring Harbor Laboratory Press, New York (2001), which has comprehensive disclosure of recombinant DNA technology.

Following expression, the anti-C5a antibody may be isolated or purified in a variety of ways known to those skilled in the art.

An anti-C5a antibody may be used as a therapeutic agent and is administered to a patient in needed thereof as any suitable formulation/composition and by any suitable route (such as by IV injection). An anti-C5a antibody may also be used as a capture antibody or a detection antibody in methods disclosed herein.

Back Disassociation ELSIA Assay Modeling

When quantifying target/efficacy biomarkers, traditional plate based ligand binding assays have potential to overestimate free analyte. Overestimation of free analyte in such situations suggests lower lack of efficacy than that which is true in vivo. Eculizumab is a mAb therapeutic approved for 2 ultra rare disease indications, and targets complement factor C5 (190 kD). Proper quantification of free C5 in the presence of drug is crucial.

The experimental evidence shows that antigen binding to ELSIA plate requires at least 30 hours for solution and plate to arrive at equilibrium.

The critical parameters are incubation time, dilution time, dilution temperature, and sample vs. assay range. Shorter plate incubation time may decrease disassociation. Cooling during two dilution steps may slow off rate $k_d$ and keep antigen-mAb and antigen-mAb-antigen from disassociating. Shorter dilution time may decrease disassociation. Dilute less may decrease disassociation. Measure neat samples if possible.

Antigen Concentration and mAb concentration (PK) data mismatch is due to: Different assay dilutions and times; Measured Antigen Concentration is over estimating free Antigen; and measured mAb (PK) is over estimating true free mAb due to disassociation from dilution and under estimating total mAb due to solution antigen.

Hemolysis modeling (using hemolytic assay for human serum samples containing C5) suggests that antigen, PK, and hemolysis (PD) data mismatch is due to: Different assay dilutions and times; Measured antigen concentration is over estimating free Antigen in hemolysis assay; Measured mAb—Eculzumab—(PK) is over estimating true free mAb due to disassociation from dilution and under estimating total mAb due to solution antigen; and Measured hemolysis is over estimating true free Antigen due to disassociation from dilution.

$$\text{kon} \qquad \text{Equilibrium Equation}$$
$$mAb + L = mAb * L$$
$$\text{koff}$$

$$K_d = 1/k_a = [mAb]_{free} \times [L]_{free} / [mAb*L]_{bound}$$

$$Kd = \frac{kon}{koff}(M)$$

$K_d$=dissociation constant, $K_a$=association constant
$K_{off}$=dissociation rate, $k_{on}$=association rate After dosing, binding of mAb to soluble L (ligand) in vivo assumed to follow law of mass action. Ex vivo conditions such as sample collection, storage, etc. may shift equilibrium to conditions different from in vivo.

$k_{off}$ values often strongly temperature and buffer sensitive. Equilibration time increases by about 30-fold at 0° C. compared to 30° C. The dissociation rate constant should always be determined under the conditions of the assay.

$L_{free}$ Measurements

Increasingly used in drug development to guide decisions; useful in dose and schedule selection. Understanding L kinetics can help define efficacious $MAb_{free}$ levels.

Certain Embodiment Methods of Quantifying Free C5A

When quantifying target/efficacy biomarkers, traditional plate based ligand binding assays have potential to overestimate free analyte. Overestimation of free analyte in such situations suggests lower lack of efficacy than that which is true in vivo. ALXN1007 is a mAb therapeutic undergoing clinical trials for treating human patients suffering from graft-vs.-host disease and targets complement factor C5a. Proper quantification of free C5a in the presence of drug is crucial.

There is no known antibody that binds specifically to C5a and does not bind specifically to C5. Thus, C5 is first removed from a sample prior to capturing and detecting free C5a in the Gyros system. C5 may be removed by incubating the sample with C5 specific antibody bound to magnetic beads and removing C5 by capturing the magnetic beads with bound C5 specific antibody and C5 with a magnet resulting in supernatant comprising C5a.

The Gyros system (Gyros AB, Uppsala, Sweden; www.gyros.com) is used in the methods disclosed herein. Since a Gyros assay passes samples along the microstructures in a matter of seconds, there may not be opportunity for back dissociation to occur. The Gyros system uses an affinity flow-through format and eliminates incubations and shortens run times. The Gyros platform uses Gyros' proprietary CD technology engineered with highly reproducible nanoliter microfluidics integrated with Gyrolab platforms, which automate immunoassays with parallel processing using laser-induced fluorescence detection. This is possible through precise, automated control of centrifugal and capillary forces which steer liquid flow through nanoliter-scale microfluidic structures contained within the CD.

Circular Bioaffy compact disc (CD) is used. PCR plates may be used for samples and reagents. Many available PCR plates may be used. The plates are sealed with foil to prevent evaporation. The capture reagent (such as a biotinylated anti-C5a antibody) enters the CD by capillary action. Hydrophobic breaks stop liquid flow. The CD is subjected to centrifugal force inside an instrument dedicated for the assay, such as a Gyrolab xPlore or Gyrolab XP. The centrifugal force drives reagents into columns inside the CD. Capture reagent binds to strepavidin-coated particles in the columns. The sample then enters the CD by capillary action and the sample applied to activated columns. The detection reagent (e.g. AlexaFluor labeled anti-C5a antibody; one that binds to a different epitope than the anti-C5a antibody used as capture reagent) then enters by capillary action and applied to columns. The columns are then scanned by laser (112 columns within 90 seconds). Rexxip A may be used for standards, QCs, samples and Rexxip F for detection Ab. Laser induced fluorescence is then used to measure the concentration or amount of the sample (e.g., C5a).

The Gyros assay uses very little sample volume (such as 4 pL) and takes very little time (such as 1.5 hours). It has a calibration range of 0.78 pM-300 pM.

This disclosure provides a method of quantitating free (unbound) human C5a complement protein (C5a) from a sample comprising:

a. removing human C5 from the sample; wherein the sample is incubated with C5 specific biotinylated antibody coupled to magnetic beads and wherein the magnetic beads coupled to C5 specific biotinylated antibody bound to human C5 are captured with a magnet;

b. binding biotinylated anti-C5a capture antibody to strepavidin-coated particles; wherein said biotinylated anti-C5a capture antibody is added by capillary action to a Gyros Bioaffy 200 CD comprising columns with the strepavidin-coated particles; wherein said CD is subjected to centrifugal force inside a Gyrolab xPlore or a Gyrolab XP instrument, thus driving the biotinylated anti-C5a capture antibody to the strepavidin-coated particles in the columns;

c. capturing the free (unbound) C5a in the sample on the capture antibody; wherein the sample after step a. is added to the CD by capillary action; wherein said CD is subjected to centrifugal force inside the Gyrolab xPlore or a Gyrolab XP instrument, thus driving the sample after step a. to the biotinylated anti-C5a capture antibody bound on the strepavidin-coated particles in the columns;

d. detecting the captured free C5a; wherein an AlexaFluor labeled anti-C5a detection antibody is added to the CD by capillary action, wherein said anti-C5a detection antibody binds C5a at a different epitope from the epitope bound by the capture antibody; wherein said CD is subjected to centrifugal force inside the Gyrolab xPlore or a Gyrolab XP instrument, thus driving the detection antibody to the free C5a bound to the capture antibody bound on the strepavidin-coated particles in the columns; and e. quantitating the captured free C5a using laser-induced fluorescence detection.

C5a in a sample, such as a serum sample from a patient treated with ALXN1007, may be free (unbound) or may be bound to ALXN1007.

Any suitable instrument for use of a Gyro assay, such as Gyrolab xPlore or Gyrolab XP, may be used.

In certain embodiments, the method further comprises calculating the concentration or amount of free C5a antibody by comparing the value obtained from step e. to a standard curve prepared from known amounts of C5a added to a C5a depleted sample. The sample with the controls is processed the same way as the patient's sample. In certain embodiments, the method further comprises calculating the concentration of free C5a antibody with the Gyros Evaluator software, or another suitable software.

In certain embodiments, the sample is obtained from a human patient. In certain further embodiments, the sample is a serum sample. In yet other embodiments, the sample is from a patient undergoing treatment with an anti-C5a antibody, such as ALXN1007. In certain embodiments, the sample is taken before treatment with ALXN1007. In other embodiments, the sample is taken after treatment with ALXN1007. The sample may be any suitable sample that may contain C5a and may be serum, plasma, blood, urine, solid sample, etc. The samples may be obtained and prepared for use according to methods known in the art.

In certain embodiments, the magnetic beads are Dynabead magnetic beads. Any suitable magnetic beads and magnets may be used.

In certain embodiments, the C5 specific antibody is biotinylated N19/8. Any suitable C5 specific antibody may be used.

In certain embodiments, the biotinylated capture antibody is ALXN1007. The biotinylated capture antibody may be any anti-C5a antibody.

In certain embodiments, the detection anti-C5a antibody is clone 2942. The detection anti-C5a antibody may be any anti-C5a antibody. The detection anti-C5a antibody in any given assay is one that recognizes a different epitope on C5a as compared to the capture antibody used in that assay; and thus does not compete for binding to C5a with the capture antibody.

In certain embodiments, Rexxip AN buffer or 1M NaCl/0.5% Tween 20 buffer is used for diluting samples and Rexxip F buffer is used for diluting the detection antibody. Any suitable buffer may be used, including slight variations on the Rexxip AN buffer, 1M NaCl/0.5% Tween 20 buffer, or Rexxip F buffer.

In certain embodiments, the Gyros instrument is primed two separate times with Bioaffy wash 1 and pH 11 buffer. Any suitable buffer may be used and priming may be skipped and may be done any suitable number of times.

Methods of conjugating an antibody with biotin or AlexaFluor are known in the art.

Exemplary Utility

The methods disclosed herein may be used for any purpose that requires quantifying the concentration or amount of free (unbound) C5a in a sample. The methods, for example, may be used to detect the concentration or amount of free (unbound) C5a in a human serum sample from a patient being treated by ALXN1007 therapy. The concentration or amount of free (unbound) C5a in such a sample would allow the patient's disease state be monitored. This assay has the advantage in such an example of quantifying free (unbound) C5a and not the C5a molecules bound to eculizumab used as therapy. ALXN1007 is undergoing clinical trials for treating human patients suffering from graft vs. host disease.

Proper quantification of free C5a is essential for a number of reasons, such as monitoring disease state, modeling, dosage selection, and label claims.

EXAMPLES

For this invention to be better understood, the following examples are set forth. These examples are for purposes of illustration only and are not be construed as limiting the scope of the invention in any manner.

Example 1. A Gyros Assay for the Quantification of Free C5a in Human Plasma

Complement protein C5a is an important component of the alternative complement cascade, and a target of Alexion drug ALXN1007. Proper quantification of this target is essential for both modeling and label claims. ALXN1007 has 60 pM affinity for C5a, but also has 5 nM affinity for C5. The affinity for C5 is based on neoepitope availability when C5 convertase cleaves C5 into C5a and C5b, and is a function of time. This low level affinity for C5 can have an additive effect on the quantitation of C5a in bioassays because like ALXN1007, there are no secondary antibodies that are specific only for C5a; they bind C5 at a lower affinity as well. If C5 is bound by ALXN1007 when the drug is used as a capture antibody in a ligand binding assay format, a proportion of the protein will be recognized and bound by an anti-C5a antibody, thus leading to over-estimation of that which is truly C5a.

The Gyrolab technology is based on assay washes, reagents, and samples spinning across microstructures on a disc at proscribed intervals. The required time for a sample to be spun across a microstructure immobilized with capture reagent is about six seconds, so theoretically there should be very little opportunity for low affinity binding of C5 when ALXN1007 is the capture reagent. Additionally, in order to further reduce the chance for C5 to be bound and have an additive effect on the assay, human plasma samples are pretreated with magnetic beads to which a C5 specific antibody is bound, therefore removing much of the C5 before it is loaded into the assay plate and disc. The bead buffer is high in salt and detergent which diminishes low affinity binding.

Materials & Methods

Materials:

Bioaffy 1000 discs, Rexxip AN buffer, Rexxip F buffer, pH 11 buffer, plate foil (Gyros US, Inc., Warren NJ)

Purified human C5a (CompTech, Tyler TX)

Biotinylated ALXN1007, biotinylated N19/8 antibody (Alexion Pharmaceuticals, New Haven CT)

AlexaFluor labeled clone 2942 (Hycult Biotech, Plymouth Meeting, PA)

96 well PCR plates, Bioaffy wash 1 (PBS with 0.1% Tween 20, 0.02% sodium azide (wash ingredients)), Dynabeads MyOne Streptavidin C, 1M NaCl/0.5% Tween 20 (buffer ingredients) (ThermoFisher, Waltham MA)

Equipment:

Gyros xPlore or XP Workstation instrument (Gyros US, Inc., Warren NJ)

Method:

The Gyros instrument is primed two separate times with Bioaffy wash 1 and pH 11 buffer, each buffer with its own station. During these prime cycles (about twenty minutes each), assay reagents, washes, and samples are prepared as described below. The number of Bioaffy 1000 discs required for the run (one for Gyros xPlore, up to five for Gyros XP Workstation) are removed from refrigerated storage and allowed to come to ambient room temperature.

Unknown human plasma samples are diluted in Dynabeads coupled to biotinylated antibody N19/8. The dilution is performed at a ratio of two parts beads to one part plasma. This dilution is performed in a round bottomed polypropylene plate for one hour at room temperature with vigorous shaking. After this one hour incubation, the plate is put onto a magnet and after two minutes the diluted plasma samples are pipetting off of the bead pellets and put on the PCR plate in their respective positions and at their required volumes. No further dilution of the unknown plasma samples is necessary.

The assay's standard curve is prepared from purified human C5a protein which is spiked into Rexxip AN buffer at 60 ng/mL and then diluted 2 fold as follows: 60 (initial spike), 30, 15, 7.5, 3.75, 1.88, 0.938, 0.469, 0.234, 0.117, and 0.058 ng/mL. The 0.058 and 60 ng/mL standard samples are anchor points. Once formulated in Rexxip AN buffer, the curve is diluted 1:2 in 1M NaCl/0.5% Tween 20 and mixed. Diluted standards are put on the PCR plate in their respective positions and at their required volumes.

Quality control (QC) samples are formulated in the same manner as standard samples. Purified human C5a is spiked into Rexxip AN buffer at 25, 5, and 0.5 ng/mL. These samples are then diluted 1:2 in 1M NaCl/0.5% Tween 20 as described for the standard curve samples. When required, samples at the limits of detection (45 ng/mL for upper limit of detection (ULOQ) and 0.120 ng/mL for lower limit of detection (LLOQ)) are formulated the same way. Diluted QCs are put on the PCR plate in their respective positions and at their required volumes.

Biotinylated capture reagent (ALXN1007) is formulated to a working concentration of 100 μg/mL in Bioaffy wash 1, and AlexaFluor labeled clone 2942 is formulated to a working concentration of 4 μg/mL in Rexxip F. Both of these reagents are placed in their respective predetermined locations on the PCR plate at their required volumes. Bioaffy wash 1 is used as the assay buffer and is loaded into respective predetermined locations on the PCR plate.

The PCR plate loaded with standards, QCs, any unknown plasma samples, assay reagents, and assay washes is sealed with foil and then loaded onto the Gyros instrument. The required number of Bioaffy 1000 discs is also loaded onto the instrument.

Assays are run on the Gyros system using the Gyros Client software. This is a three-step assay (capture, analyte, detect) whereby capture antibody, sample, and detection antibody are added at programmed intervals and between intermittent wash steps. Assay run time is about one hour per disc. Data is processed by the Gyros Evaluator software, or can be exported for import into a laboratory information system (LIMS) such as Watson. This assay uses a 5PL curve fit with response weighting and a 1% PMT setting. Due to the differences in dilution of standard curve and plasma samples (1:1 for standards, 1:2 for plasma samples), a dilution factor of 1.5 is applied to any plasma results.

Results

The Gyros assay for the quantification of free C5a in human plasma has a dynamic range of 0.120-45 ng/mL, which translates to 0.180-67.5 ng/mL in plasma after dilution factor correction. The effects of the bead treatment for plasma samples are seen in three ways: first, in reduction of available C5 to measure on the Gyros assay for the quantification of free C5 using eculizumab as the capture reagent (as proscribed in that test method); second, in the reduction of C5 binding by ALXN1007 when it is used as capture antibody in place of eculizumab in the same assay format; and third, in the amount of C5a bound by the Gyros free C5a assay. Although the differences between the two bead buffers (Rexxip AN or 1M NaCl/0.50 Tween 20) are minimal in terms of free C5a measurement, there is an apparent difference in terms of free C5 measured. For this reason, the 1M NaCl/0.5% Tween 20 buffer is the diluent of choice for bead treatment of plasma samples, and the assay diluent for both standard and QC samples.

TABLE 1

Bead Treatment Effects on Free C5 (Eculizumab Capture and ALXN1007 Capture) and Free C5a Using Either Rexxip AN buffer or 1M NaCl/0.5% Tween 20 as Bead Buffer

| Sample | Treatment ratio, vol beads:vol matrix sample | Free C5a result, ng/mL | Free C5 result, μg/mL (ALXN1007 capture) | Free C5 result, μg/mL (Eculizumab capture) |
|---|---|---|---|---|
| 2 | NA | 3.54 | 5.11 | 65.8 |
| 02 beads Rexxip buffer | 2:1 | 1.84 | 0.68 | 14.1 |
| 02 beads 1M NaCl 0.5% Tw20 | 2:1 | 1.79 | 0.52 | 12.9 |
| 3 | NA | 3.74 | 4.63 | 61.3 |
| 03 beads Rexxip buffer | 2:1 | 2.39 | 0.61 | 9.2 |
| 03 beads 1M NaCl 0.5% Tw20 | 2:1 | 2.32 | 0.34 | 6.4 |
| 4 | NA | 3.25 | 5.79 | 90.6 |
| 04 beads Rexxip buffer | 2:1 | 1.53 | 0.68 | 13.2 |
| 04 beads 1M NaCl 0.5% Tw20 | 2:1 | 1.26 | 0.37 | 9.5 |
| 5 | NA | 8.37 | 4.04 | 56.2 |
| 05 beads Rexxip buffer | 2:1 | 5.29 | 0.35 | 7.9 |
| 05 beads 1M NaCl 0.5% Tw20 | 2:1 | 5.11 | 0.31 | 6.3 |

Selectivity of a target biomarker assay is an important assay parameter. Table 2 shows data for donor plasma spiked with 5 ng/mL of purified C5a reference material, which has an additive effect on the measurement of the endogenous C5a levels already in each sample. The Gyros assay accurately measured purified C5a spiked into samples containing the endogenous counterpart at both 1% and 5% PMT settings for 80% of the small sample size tested.

TABLE 2

Gyros Selectivity for Free C5a in Human Plasma (ng/mL)

| | Endogenous | Theoretical End + Spike | Actual End + Spike | % Recovery |
|---|---|---|---|---|
| 1% PMT | | | | |
| Donor 1 | 5.56 | 10.1 | 6.7 | 66.3 |
| Donor 2 | 5.05 | 9.6 | 8.9 | 92.7 |
| Donor 3 | 5.17 | 9.7 | 9.6 | 99.0 |
| Donor 4 | 6.41 | 10.9 | 9.8 | 89.9 |
| Donor 5 | 2.75 | 7.5 | 6.75 | 90.0 |
| 5% PMT | | | | |
| Donor 1 | 5.46 | 10.0 | 6.9 | 69.0 |
| Donor 2 | 4.95 | 9.5 | 8.7 | 91.6 |
| Donor 3 | 5.02 | 9.6 | 9.5 | 99.0 |
| Donor 4 | 6.32 | 10.8 | 9.7 | 89.8 |
| Donor 5 | 2.66 | 7.4 | 6.6 | 89.2 |

Parallelism is an important element to determine in a biomarker assay, as it can be a determination of the goodness of fit of a surrogate matrix (here, Rexxip AN buffer) standard curve and its purified reference material (here, purified human C5a). By pretreating matrix samples with extra dilutions prior to the proscribed bead treatment, parallelism can show differences in assay response between the surrogate curve and unknown samples measured from it. FIG. 1 shows parallelism results for five donor plasmas. These data suggest that the assay has parallelism, and that the surrogate curve is appropriate.

Discussion

The Gyros assay for the quantification of free C5a in human plasma has a dynamic range of 0.120-45 ng/mL, which translates to 0.180-67.5 ng/mL in plasma after dilution factor correction.

The selectivity and parallelism of the assay show that the surrogate matrix and reference material are appropriate for the endogenous counterpart being measured in human plasma.

Data from endogenous plasma samples run on the Gyros assay with and without bead treatment suggest that the Gyros assay reduces the amount of low affinity C5 binding that can have an additive effect on results. This bead treatment, together with the already very brief sample incubation time of the Gyros technology, yields an assay for the quantification of free C5a that is more specific than other methods.

Example 2. A Gyros Assay for the Quantification of Free C5a in Human Plasma

ALXN1007 is a humanized mAb targeting C5a/C5a des-Arg (10.4 kD, alternative pathway). It is scheduled for an adaptive Phase II/III clinical trial for GVHD (graft vs. host disease).

Accurate and sensitive quantitation of biomarker (human C5a) is needed for proper modeling/efficacy. The challenges are ALXN1007 also binds C5, albeit a few orders of magnitude lower than C5a (5 nM vs. 60 pM); this binding of C5 is a function of time and neoepitope availability. There really are no antibodies that bind only C5a and not C5 to some degree. The additive effect impacts sensitivity of assay.

Since the typical Gyros assay passes samples along the microstructures in a matter of seconds, there may be no real opportunity for ALXN1007 to bind C5.

Figure 2:
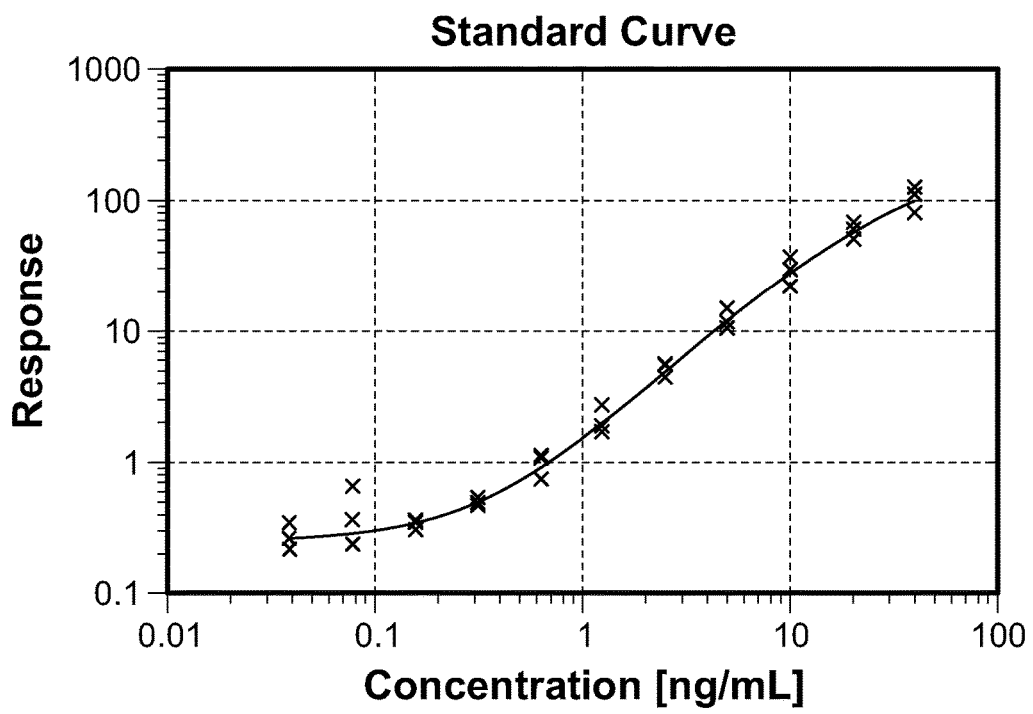
FIG. 2 is an example of a standard curve done in triplicates.

FIG. 2 and Table 3 show the importance of triplicates.

TABLE 3

| Standard Sample | ng/mL | Response |
| --- | --- | --- |
| Standard des arg_Rexxip HN_8 | 0.313 | 0.546586 |
| Standard des arg_Rexxip HN_8 | 0.313 | 0.491027 |
| Standard des arg_Rexxip HN_8 | 0.313 | 0.46775 |
| Standard des arg_Rexxip HN_7 | 0.625 | 1.10201 |
| Standard des arg_Rexxip HN_7 | 0.625 | 1.13298 |
| Standard des arg_Rexxip HN_7 | 0.625 | 0.747166 |
| Standard des arg_Rexxip HN_6 | 1.25 | 2.81148 |
| Standard des arg_Rexxip HN_6 | 1.25 | 1.93956 |
| Standard des arg_Rexxip HN_6 | 1.25 | 1.75661 |
| Standard des arg_Rexxip HN_5 | 2.5 | 5.71828 |
| Standard des arg_Rexxip HN_5 | 2.5 | 5.66135 |
| Standard des arg_Rexxip HN_5 | 2.5 | 4.54024 |
| Standard des arg_Rexxip HN_4 | 5 | 15.0539 |
| Standard des arg_Rexxip HN_4 | 5 | 11.754 |
| Standard des arg_Rexxip HN_4 | 5 | 10.6638 |
| Standard des arg_Rexxip HN_3 | 10 | 37.5782 |
| Standard des arg_Rexxip HN_3 | 10 | 30.0124 |
| Standard des arg_Rexxip HN_3 | 10 | 22.7817 |
| Standard des arg_Rexxip HN_2 | 20 | 70.1262 |
| Standard des arg_Rexxip HN_2 | 20 | 62.216 |
| Standard des arg_Rexxip HN_2 | 20 | 51.5977 |
| Standard des arg_Rexxip HN_1 | 40 | 128.406 |
| Standard des arg_Rexxip HN_1 | 40 | 113.725 |
| Standard des arg_Rexxip HN_1 | 40 | 83.3196 |

Gyros Assay Parameters
Capture Ab @ 100 µg/mL
Detect Ab @ 4 µg/mL
Purified human C5a as reference material
Rexxip AN for formulation of standards and QCs
Bioaffy 1000 nL discs
Rexxip AN for dilution of standards, QCs, samples (sample dilution 2)
Rexxip F for detection Ab
Wash 1: Bioaffy wash 1
Wash 2: pH 11 buffer
3 step assay (C-A-D)
PMT 1%

Current plate based ECL assay format has dynamic range of 0.280-40.0 ng/mL
Sample dilution 1:4
Proposed curve range 0.117-60.0 ng/mL To further reduce binding to C5, C5 protein molecules from the sample are removed with Dynabeads bound to biotinylated anti-C5 antibody. Final diluent of coupled beads is Rexxip AN. Pre-incubation of coupled beads with matrix samples for C5 depletion.

FIG. 3 shows bead effect on C5a and C5. FIG. 4 shows Bead Effect—Rexxip AN vs 1M NaCl/0.5% Tween 20; Not much effect on C5a binding, but drug binding of C5 appears to be affected.

Updated Free C5a Assay Parameters
Capture Ab @ 100 µg/mL
Detect Ab @ 4 µg/mL
Purified human C5a as reference material
Rexxip AN for formulation of standards and QCs
Bioaffy 1000 nL discs
1M NaCl/0.5% Tween 20 for dilution of standards and QCs (MRD 2)
Coupled Dynabeads (20 µg/mL Ab) in 1M NaCl/0.5% Tween 20 for dilution of matrix samples, 2:1 ratio, room temperature incubation for one hour with shaking
Rexxip F for detection Ab
Wash 1: Bioaffy wash 1
Wash 2: pH 11 buffer
3 step assay (C-A-D)
PMT 1%
Proposed curve range 0.117-60.0 ng/mL
In matrix LLOQ 0.176

FIG. 5 shows free C5a early bead treatment selectivity and FIG. 1 shows free C5a early bead treatment parallelism.

Most assays that use drug to capture free target have potential to over-estimate that which truly is free. Gyros enables more accurate quantification of target biomarkers due to truncated sample incubation. For the same reason, Gyros (alone or in conjunction with sample treatment) can also help reduce non-specific or low affinity binding.

Other Embodiments

The foregoing description discloses only exemplary embodiments of the invention.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the appended claims. Thus, while only certain features of the invention have been illustrated and described, many modifications and changes will occur to those skilled in the art. It is therefore to be understood that the appended claims are intended to cover all such modifications and changes as fall within the true spirit of the invention.

TABLE 4

| SEQUENCE SUMMARY | |
|---|---|
| SEQ ID NO: | Amino Acid Sequence |
| SEQ ID NO: 1<br>BNJ383<br>Full light chain<br>sequence with<br>signal peptid | MDMRVPAQLLGLLLLWLRGARCDIQMTQSPSSLSASVGDRVTITCRASE<br>SVDSYGNSFMHWYQQKPGKAPKLLIYRASNLESGVPSRFSGSGSGTDFT<br>LTISSLQPEDFATYYCQQSNEDPYTFGGGTKVEIKRTVAAPSVFIFPPS<br>DEQLKSGTASVVCLLNNFYPREAKVQWKVDNALQSGNSQESVTEQDSKD<br>STYSLSSTLTLSKADYEKHKVYACEVTHQGLSSPVTKSFNRGEC |
| SEQ ID NO: 2<br>BNJ383<br>Full light chain<br>sequence without<br>signal peptide | DIQMTQSPSSLSASVGDRVTITCRASESVDSYGNSFMHWYQQKPGKAPK<br>LLIYRASNLESGVPSRFSGSGSGTDFTLTISSLQPEDFATYYCQQSNED<br>PYTFGGGTKVEIKRTVAAPSVFIFPPSDEQLKSGTASVVCLLNNFYPRE<br>AKVQWKVDNALQSGNSQESVTEQDSKDSTYSLSSTLTLSKADYEKHKVY<br>ACEVTHQGLSSPVTKSFNRGEC |
| SEQ ID NO: 3<br>BNJ383<br>Light chain<br>variable region<br>sequence signal<br>peptide | MDMRVPAQLLGLLLLWLRGARC |
| SEQ ID NO: 4<br>BNJ383<br>Light chain<br>variable region<br>sequence | DIQMTQSPSSLSASVGDRVTITCRASESVDSYGNSFMHWYQQKPGKAPK<br>LLIYRASNLESGVPSRFSGSGSGTDFTLTISSLQPEDFATYYCQQSNED<br>PYTFGGGTKVEIKR |
| SEQ ID NO: 5<br>BNJ383<br>Light chain<br>variable region<br>sequence Kabat<br>LCDR1 | RASESVDSYGNSFMH |
| SEQ ID NO: 6<br>BNJ383<br>Light chain<br>variable region<br>sequence Kabat<br>LCDR2 | RASNLES |
| SEQ ID NO: 7<br>BNJ383<br>Light chain<br>variable region<br>sequence Kabat<br>LCDR3 | QQSNEDPYT |
| SEQ ID NO: 8<br>BNJ383<br>Light chain<br>constant region<br>sequence | TVAAPSVFIFPPSDEQLKSGTASVVCLLNNFYPREAKVQWKVDNALQSG<br>NSQESVTEQDSKDSTYSLSSTLTLSKADYEKHKVYACEVTHQGLSSPVT<br>KSFNRGEC |
| SEQ ID NO: 9<br>BNJ383<br>Full heavy chain<br>sequence with<br>signal peptide | MDWTWRVFCLLAVAPGAHSQVQLVQSGAEVKKPGASVKVSCKASGYTFT<br>DYSMDWVRQAPGQGLEWMGAIHLNTGYTNYNQKFKGRVTMTRDTSTSTV<br>YMELSSLRSEDTAVYYCARGFYDGYSPMDYWGQGTTVTVSSASTKGPSV<br>FPLAPCSRSTSESTAALGCLVKDYFPEPVTVSWNSGALTSGVHTFPAVL<br>QSSGLYSLSSVVTVPSSNFGTQTYTCNVDHKPSNTKVDKTVERKCCVEC<br>PPCPAPPVAGPSVFLFPPKPKDILMISRTPEVICVVVDVSQEDPEVQFN<br>WYVDGVEVHNAKTKPREEQFNSTYRVVSVLTVLHQDWLNGKEYKCKVSN<br>KGLPSSIEKTISKAKGQPREPQVYTLPPSQEEMTKNQVSLICLVKGFYP<br>SDIAVEWESNGQPENNYKTIPPVLDSDGSFFLYSRLTVDKSRWQEGNVF<br>SCSVMHEALHNHYTQKSLSLSLGK |
| SEQ ID NO: 10<br>BNJ383<br>Full heavy chain<br>sequence without<br>signal peptide | QVQLVQSGAEVKKPGASVKVSCKASGYTFTDYSMDWVRQAPGQGLEWMG<br>AIHLNIGYTNYNQKFKGRVTMTRDTSTSTVYMELSSLRSEDTAVYYCAR<br>GFYDGYSPMDYWGQGTTVTVSSASTKGPSVFPLAPCSRSTSESTAALGC<br>LVKDYFPEPVTVSWNSGALTSGVHTFPAVLQSSGLYSLSSVVTVPSSNF<br>GTQTYTCNVDHKPSNTKVDKTVERKCCVECPPCPAPPVAGPSVFLFPPK<br>PKDTLMISRTPEVTCVVVDVSQEDPEVQFNWYVDGVEVHNAKTKPREEQ<br>FNSTYRVVSVLTVLHQDWLNGKEYKCKVSNKGLPSSIEKTISKAKGQPR<br>EPQVYTLPPSQEEMTKNQVSLTCLVKGFYPSDIAVEWESNGQPENNYKT<br>TPPVLDSDGSFFLYSRLTVDKSRWQEGNVFSCSVMHEALHNHYTQKSLS<br>LSLGK |

TABLE 4-continued

SEQUENCE SUMMARY

| SEQ ID NO: | Amino Acid Sequence |
| --- | --- |
| SEQ ID NO: 11<br>BNJ383<br>Heavy chain<br>variable region<br>sequence signal<br>peptide | MDWTWRVFCLLAVAPGAHS |
| SEQ ID NO: 12<br>BNJ383<br>Heavy chain<br>variable region<br>sequence | QVQLVQSGAEVKKPGASVKVSCKASGYTFTDYSMDWVRQAPGQGLEWMG<br>AIHLNIGYTNYNQKFKGRVTMTRDTSTSTVYMELSSLRSEDTAVYYCAR<br>GFYDGYSPMDYWGQGTTVTVSS |
| SEQ ID NO: 13<br>BNJ383<br>Heavy chain<br>variable region<br>sequence Kabat<br>HCDR1 | DYSMD |
| SEQ ID NO: 14<br>BNJ383<br>Heavy chain<br>variable region<br>sequence Kabat<br>HCDR2 | AIHLNTGYTNYNQKFKG |
| SEQ ID NO: 15<br>BNJ383<br>Heavy chain<br>variable region<br>sequence Kabat<br>HCDR3 | GFYDGYSPMDY |
| SEQ ID NO: 16<br>BNJ383<br>Heavy chain<br>constant region<br>sequence | ASTKGPSVFPLAPCSRSTSESTAALGCLVKDYFPEPVTVSWNSGALTSG<br>VHTFPAVLQSSGLYSLSSVVTVPSSNFGTQTYTCNVDHKPSNTKVDKTV<br>ERKCCVECPPCPAPPVAGPSVFLFPPKPKDTLMISRTPEVTCVVVDVSQ<br>EDPEVQFNWYVDGVEVHNAKTKPREEQFNSTYRVVSVLTVLHQDWLNGK<br>EYKCKVSNKGLPSSIEKTISKAKGQPREPQVYTLPPSQEEMTKNQVSLT<br>CLVKGFYPSDIAVEWESNGQPENNYKTTPPVLDSDGSFFLYSRLTVDKS<br>RWQEGNVFSCSVMHEALHNHYTQKSLSLSLGK |
| SEQ ID NO: 17<br>Human C5a<br>protein | TLQKKIEEIAAKYKHSVVKKCCYDGACVNNDETCEQRAARISLGPRCIK<br>AFTECCVVASQLRANISHKDMQLGR |
| SEQ ID NO: 18<br>Desarginated<br>human C5a<br>protein | TLQKKIEEIAAKYKHSVVKKCCYDGACVNNDETCEQRAARISLGPRCIK<br>AFTECCVVASQLRANISHKDMQLG |

What is claimed is:

1. A method of quantitating unbound human C5a complement protein (C5a) from a sample comprising:
   a. removing human C5 from the sample; wherein the sample is incubated with C5 specific biotinylated antibody coupled to magnetic beads and wherein the magnetic beads coupled to C5 specific biotinylated antibody bound to human C5 are captured with a magnet;
   b. binding biotinylated anti-C5a capture antibody to streptavidin coated particles; wherein said biotinylated anti-C5a capture antibody is added by capillary action to a compact disc comprising columns with the streptavidin coated particles; wherein said compact disc is subjected to centrifugal force inside an instrument, thus driving the biotinylated anti-C5a capture antibody to the streptavidin coated particles in the columns;

c. capturing the unbound C5a in the sample on the capture antibody; wherein the sample after step a. is added to the compact disc by capillary action;

wherein said compact disc is subjected to centrifugal force inside the instrument, thus driving the sample after step a. to the biotinylated anti-C5a capture antibody bound to the streptavidin coated particles in the columns;

d. detecting the captured C5a; wherein an Alexa_Fluor labeled anti-C5a detection antibody is added to the compact disc by capillary action, wherein said anti-C5a detection antibody binds C5a at a different epitope from the epitope bound by the capture antibody; wherein said compact disc is subjected to centrifugal force inside the instrument, thus driving the detection antibody to the C5a bound to the capture antibody bound to the streptavidin coated particles in the columns, wherein 1M NaCl/0.5% Tween 20 buffer is used; and e. quantitating the captured C5a using laser-induced fluorescence detection.

2. The method of claim 1, further comprising calculating the concentration or amount of C5a antibody by comparing the value obtained from step e. to a standard curve prepared from known amounts of C5a added to a C5a depleted sample.

3. The method of claim 1, further comprising calculating the concentration of free anti-C5a antibody.

4. The method of claim 1, wherein the sample is obtained from a human patient.

5. The method of claim 4, wherein said sample is a serum sample or a plasma sample.

6. The method of claim 1, wherein the patient has been treated with an anti-C5a antibody.

7. The method of claim 6, wherein the patient has been treated with an antibody comprising heavy chain CDR1, CDR2, CDR3 domains having the sequences of SEQ ID NOs: 13, 14, 15 and light chain CDR1, CDR2, and CDR3 domains having the sequences of SEQ ID NOs: 5, 6, and 7.

8. The method of claim 7, wherein the patient has been treated with an antibody comprising heavy and light chains having the sequences of SEQ ID NOs:10 and 2.

9. The method of claim 1, wherein the magnetic beads are Dynabead magnetic beads.

10. The method of claim 1, wherein the biotinylated capture antibody comprises heavy chain CDR1, CDR2, CDR3 domains having the sequences of SEQ ID NOs: 13, 14, 15 and light chain CDR1, CDR2, and CDR3 domains having the sequences of SEQ ID NOs: 5, 6, and 7.

11. The method of claim 10, wherein the biotinylated capture antibody comprises heavy and light chains having the sequences of SEQ ID NOs:10 and 2.

12. The method of claim 1, wherein 1M NaCl/0.5% Tween 20 buffer is used as a bead buffer.

13. The method of claim 1, further comprising priming the compact disc two separate times with phosphate buffered saline wash solution.

14. The method of claim 1, wherein step (a) uses a buffer of about 1M NaCl and about 0.5% Tween 20.

15. The method of claim 1, further comprising depleting C5 with an anti-C5 antibody.

16. The method of claim 1, wherein the instrument has a dynamic range between 0.180-67.5 ng/mL in plasma for the anti-C5a antibody after dilution factor correction.

* * * * *